United States Patent

Ferguson et al().

[11] 3,968,239
[45] July 6, 1976

[54] FUNGICIDAL COMPOSITIONS CONTAINING A PHTHALONITRILE

[75] Inventors: Fred E. Ferguson; Robert J. Bell, both of Marysville, Ohio

[73] Assignee: O. M. Scott & Sons Company, Marysville, Ohio

[22] Filed: Mar. 7, 1975

[21] Appl. No.: 556,488

[52] U.S. Cl. .............................. 424/304; 424/341
[51] Int. Cl.² ..................... A01N 9/20; A01N 9/24
[58] Field of Search ........................... 424/304, 341

[56] References Cited
UNITED STATES PATENTS
3,290,353  12/1966  Battershell et al. ............. 424/304 X OTHER PUBLICATIONS
Chemical Abstracts, 61:16715b, (1964).
Chemical Abstracts, 8th coll. subject index (1967–1971).
Chemical Abstracts, 74:124316e, (1971).

Primary Examiner—Leonard Schenkman
Attorney, Agent, or Firm—J. B. Raden; H. J. Holt

[57] ABSTRACT

A fungicide composition particularly effective for the control of leafspot and dollarspot comprising a mixture in granular form of (a) a phthalonitrile of the formula

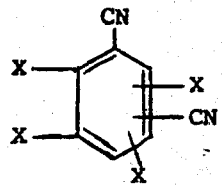

wherein each X is selected from the group consisting of hydrogen, chlorine, fluorine and bromine with at least one X being other than hydrogen, (b) for each 1275 grams of the phthalonitrile, from about 200 to 1800 ml of octyl phenoxy polyethoxy ethanol having 9 to 10 oxyethylene groups, and (c) a carrier to which the fungicide is adhered, the carrier having a bulk density of at least 20 lbs. per cubic foot.

8 Claims, No Drawings

FUNGICIDAL COMPOSITIONS CONTAINING A PHTHALONITRILE

This invention relates to a fungicide composition and to a process of treating plants with the fungicide to control the formation of disease therein.

Fungicides effective for the control of leafspot and dollarspot on plants are known. However, many are based on mercury containing compounds, such as phenyl mercuric acetate, and the use of these compounds is being significantly reduced by governmental regulations. Another known leafspot fungicide is shown in U.S. Pat. No. 3,331,735 which discloses the use of certain phthalonitriles as fungicides. However, control of a variety of fungi on turf grasses has not been satisfactory with such nitrile compounds in granular form on certain widely-used carriers. In the case of, for example, ground corncobs, a desirable carrier for these fungicides, the active fungicide apparently does not come off the carrier and the desired control through foliar application is not obtained.

It is accordingly a principal object of this invention to provide a phthalonitrile fungicide composition which may be effectively used with particulate carriers with which it has previously been ineffective in granular form.

It is an additional object of the present invention to provide a fungicide formulation containing phthalonitrile and a process for its use which effectively controls a variety of fungi including leafspot and dollarspot in plants.

The foregoing and other objects of the invention are achieved by the addition to the phthalonitrile fungicide of an octyl phenoxy polyethoxy ethanol having 9 to 10 oxyethylene groups. The latter additive is commercially available as a nonionic surface active agent under the trademark Triton X-100. Triton surfactants have been previously suggested as emulsifying agents for insecticides and herbicides. However, the unusual effectiveness of the phthalonitrile fungicide in combination with Triton X-100, particularly in the control of leafspot and dollarspot, is totally unpredictable from a knowledge of the results previously achieved with either the fungicide or the Triton X-100 compound when used for its known surfactant properties. Moreover, the unique results obtainable with Triton X-100 are not obtainable with other Triton compounds, despite their chemical similarity and their closely related physical and chemical properties.

Specifically, the invention is directed to a fungicidal composition in granular form comprising a mixture of (a) a phthalonitrile of the formula

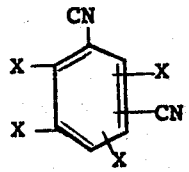

wherein each X is selected from the group consisting of hydrogen, chlorine, fluorine and bromine with at least one X being other than hydrogen, (b) for each 1275 grams of the phthalonitrile, from about 200 to 1800 ml of octyl phenoxy polyethoxy ethanol having 9 to 10 oxyethylene groups, and (c) a carrier to which the fungicide is adhered, said carrier having a bulk density of at least 20 pounds per cubic foot.

Based upon the weight of fungicide typically used to treat 10,000 sq. ft. of turf or plant area, a preferred formulation of the invention is a mixture in granular form of (a) 1275 grams of tetrachloroisophthalonitrile as the active fungicidal ingredient, (b) from 450 to 1200 milliliters of octyl phenoxy polyethoxy ethanol having an average of 9 to 10 oxyethylene groups, (c) from 200 to 1800, preferably 600 to 1600, milliliters of a lower aliphatic glycol sticking agent, and (d) a particulate or granular carrier, having the foregoing density. The formulations are, as indicated, stated in terms of an amount of fungicide typically used to treat 10,000 sq. ft. of turf area. Obviously, other amounts of the fungicide may be used. Other amounts of the active fungicide would, of course, require proportionately more or less of the other ingredients. The glycol and Triton X-100 additive are liquids and thus are expressed in terms of volume rather than by weight. Normally, the weight of carrier will be in excess of the weight of fungicide, preferably an amount ranging from 4 to 16 times the amount of the phthalonitrile. However, the amount of carrier is not critical. It may be used in any amount sufficient to give a flowable composition.

The advantages of the invention are achieved only with relatively dense carriers, — i.e., those having a bulk density greater than 20 lbs./cu. ft. Such carriers are particularly effective for use in rotary-type spreaders. The use, for example, of the well known carrier vermiculite with Triton X-100 produces results essentially no better than the same granular compositions without the Triton X-100 additive. A preferred carrier is particulate corncob which has a bulk density of from 26 to 30 lbs./cu. ft. and typically is from 10–40 U.S. sieve size. Other useful carriers with the requisite density are clays (34–40 lbs./cu. ft.), diatomaceous earth (21–24 lbs./cu. ft.) and walnut and pecan shells (up to 40 lbs/cu. ft.). Others will readily occur to those skilled in the art.

Tetrachloroisophthalonitrile is commercially available under the trademark "Daconil 2787". The preparation of this and other phthalonitriles within the scope of the invention is disclosed in U.S. Pat. No. 3,290,353. The lower aliphatic glycol sticking agents function to adhere the fungicide to the carrier in order to obtain a homogenious composition. The Triton X-100 additive is miscible with the lower aliphatic glycols, i.e. glycols with from two to six carbons such as ethylene, propylene, diethylene, dipropylene and hexylene glycol. Examples of other sticking agents useful in the granular formulations of the invention may be found in U.S. Pat. No. 3,705,794, assigned to the present assignee, the disclosure of which is hereby incorporated by reference. Triton X-100 is commercially available as a water soluble liquid. It has a viscosity of 240 centipoises at 25°C/25°C and a specific gravity of 1.065 — average 8.9 lbs. per gallon.

The compositions are prepared by mixing together the glycol sticking agent and the Triton X-100. The phthalonitrile, normally in a 75% formulation (25% inert ingredients), is mixed with the carrier and, while mixing, the glycol-Triton X-100 mixture is sprayed onto the solids mixture. The compositions of the invention are applied to turf in granular form by, for example, use of a lawn spreader at a setting which will apply a maximum of 25 lbs., but preferably 12.25 lbs., of active phthalonitrile fungicide per acre of turf. A smaller amount per acre of the composition may, of course, be used depending on the extent of fungus activity and frequency of application.

The following examples illustrate the practice of the invention.

EXAMPLE 1

A granular formulation was prepared from the following ingredients:

| | |
|---|---|
| tetrachloroisophthalonitrile (75% active) | 1701 gms. |
| Triton X-100 | 950 mls. |
| hexylene glycol | 900 mls. |
| ground corncob | 13,608 gms. |

The formulation was prepared by mixing together the glycol sticking agent with the Triton X-100. The phthalonitrile was fed dry into a blender containing the ground corn cob while the blender was agitating. Simultaneously, the glycol-Triton X-100 mixture was sprayed onto the solids mixture. The solution mixture was heated to 100°F. to aid in pumping.

Field tests were run to determine the effectiveness of the formulation of Example 1 and to compare it with other formulations, identical in all respects except for the substitution of the same amounts of other Triton compounds as the additive in place of Triton X-100. In addition, tests were made of a formulation with no additive and of a formulation with the additive but omitting the fungicide. The tests were run on Kentucky bluegrass infested with leafspot (*Helminthosporium vagans*) and bentgrass infested with dollarspot (*Sclerotinia homoeocarpa*) fungus. The tests were conducted by applying the formulations at the rate of 12.25 pounds of active phthalonitrile per acre - or equivalent amounts of the remaining ingredients where the fungicide was omitted. Plots of Kentucky bluegrass and bentgrass were randomized, replicated and treated on either a biweekly or weekly schedule. Granular formulations were applied by a Scott spreader at a setting to deliver 12.25 lbs./acre to moist turfgrasses. Observations of plots were noted as percent disease coverage in the case of leafspot or, for dollarspot, number of infection centers per plot from which percent control was calculated.

The results of the tests on dollarspot control are set forth in the following Table I. In this table, the various formulations were identical to Example 1 except for the substitution of the same amount of the following additives for the Triton X-100 compound:

Octyl phenoxy polethoxy ethanol having an average of 5 oxethylene groups (Triton X-45).

Nonyl phenoxy polyethoxy ethanol having an average of 5 oxyethylene groups (Triton N-57).

Octyl phenoxy polyethoxy ethanol having an average of 12 - 13 oxethylene groups (Triton X-102).

Octyl phenoxy polyethoxy ethanol having an average of 7 - 8 oxyethylene groups (Triton X-114).

Nonyl phenoxy polyethoxy ethanol having an average of 16 oxyethylene groups (Triton X-165).

Nonyl phenoxy polyethoxy ethanol having an average of 30 oxyethylene groups (X-305).

Nonyl phenoxy polyethoxy ethanol having an average of 9 to 10 oxyethylene groups (Triton N-101).

Example 9 contained a fungicide but the Triton X-100 additive was omitted.

TABLE I

| | | Dollarspot Control |
|---|---|---|
| Example | Additive | % Control |
| 1 | Triton X-100 | 95 |
| 2 | Triton X-45 | 84 |
| 3 | Triton N-57 | 71 |
| 4 | Triton X-102 | 90 |
| 5 | Triton X-114 | 71 |
| 6 | Triton X-165 | 61 |
| 7 | Triton X-305 | 53 |
| 8 | Triton X-101 | 69 |
| 9 | None | 72 |

Table II shows the results of tests, carried out as in Table I, for leafspot control. Example 10 is the same formulation as Example 1, Examples 11-15 contain other Triton additives or no additive at all. In Example 16, the Triton X-100 additive was included but the fungicide was omitted.

TABLE II

| | Leafspot Control | |
|---|---|---|
| Example | Additive | % Control |
| 10 | Triton X-100 | 93 |
| 11 | Triton X-45 | 80 |
| 12 | Triton N-57 | 0* |
| 13 | Triton X-102 | 0* |
| 14 | Triton X-114 | 30 |
| 15 | None | 0 |
| 16 | Triton X-100 | 39 |

*Initially Example 12 achieved 30% control and Example 13 achieved 60% control, but control did not extend to the conclusion of the tests.

Table I and II show that formulations containing in combination the phthalonitrile of the invention and the Triton X-100 additive were considerably more effective in controlling dollarspot and leafspot fungus than either the fungicide alone, the additive alone or combinations of the fungicide and other Triton compounds. While Example 4, containing Triton X-102, obtained moderately acceptable results with dollarspot, the same formulation was totally ineffective for leafspot (Example 13).

In addition to being a highly effective fungicide for leafspot and dollarspot, the fungicide composition is also effective against a number of other fungi including brown patch. It also has proven to have greater activity than other phthalonitrile granular formulations at lower rates of application. In granular form, the compositions of the invention have greater activity than other phthalonitrile granular formulations at the same application rate and a longer residual effect than other granulars or spray. It has also been found that considerably less dew is formed on grass for periods up to 5 days after application of the granular form of the present compositions — an important advantage since dew is conducive to the growth and spread of fungi.

We claim:

1. A fungicidal composition in granular form comprising a mixture of (a) tetrachloroisophthalonitrile, (b) for each 1275 grams of the phthalonitrile, from about 200 to 1800 ml of octyl phenoxy polyethoxy ethanol having 9 to 10 oxyethylene groups, and (c) a carrier to which the fungicide is adhered, said carrier having a bulk density of at least 20 lbs. per cu. ft.

2. The composition of claim 1 in which the carrier is ground corncob.

3. The composition of claim 1 containing from 200 to 1800 ml. of a sticking agent.

4. The composition of claim 3 in which the sticking agent is hexylene glycol.

5. A process for treating plants to control leafspot and dollarspot fungal disease therein comprising applying to said plants a mixture in granular form comprising (a) 1275 grams of tetrachloroisophthalonitrile, (b) from about 200 to 1800 ml. of octyl phenoxy polyethoxy ethanol having 9 to 10 oxyethylene groups, and (c) a carrier, having a bulk density of at least 20 lbs. per cu. ft., to which the fungicide is adhered, said amounts being based upon applying said mixture to 10,000 sq. ft. of plant area.

6. The process of claim 5, in which the carrier is corncob.

7. The process of claim 5 containing from 200 to 1800 ml. of a sticking agent.

8. The process of claim 5 in which the mixture is applied to turf to control leafspot fungus therein.

* * * * *